United States Patent [19]
Kondo et al.

[11] Patent Number: 5,457,996
[45] Date of Patent: Oct. 17, 1995

[54] RECEIVING BEAM FORMER AND AN ULTRASONIC IMAGING SYSTEM USING THE SAME

[75] Inventors: Shin-ichi Kondo, Kashiwa; Hiroshi Kanda, Tokorozawa; Kageyoshi Katakura, Tokyo; Ryuichi Shinomura, Higashimatsuyama; Yuichi Miwa, Hachioji, all of Japan

[73] Assignee: Hitachi Medical Corporation, Tokyo, Japan

[21] Appl. No.: 64,925

[22] Filed: May 24, 1993

[30] Foreign Application Priority Data

May 25, 1992 [JP] Japan .................... 4-156124

[51] Int. Cl.$^6$ .................................... G01N 29/00
[52] U.S. Cl. .................................... 73/625; 73/621
[58] Field of Search .................... 73/618, 620, 617, 73/622, 626

[56] References Cited

U.S. PATENT DOCUMENTS

| | | | |
|---|---|---|---|
| 4,679,176 | 7/1987 | Ogawa et al. | 367/119 |
| 4,841,491 | 6/1989 | Kondo et al. | 367/103 |
| 5,001,678 | 3/1991 | Fukuoka et al. | 73/626 |
| 5,228,007 | 7/1993 | Murakami et al. | 73/617 |

Primary Examiner—Hezron E. Williams
Assistant Examiner—Max H. Noori
Attorney, Agent, or Firm—Antonelli, Terry, Stout & Kraus

[57] ABSTRACT

A receiving beamformer is provided which simultaneously generates a plurality of receiving beam signals corresponding to receiving beams of a plurality of directions on the basis of signals received by an array of vibrator elements for receiving an ultrasonic wave. This receiving beamformer includes a variable amplifying unit for amplifying the received signals in accordance with the depth of measurement to produce output signals, an A/D converting unit for converting the output signals from the variable amplifying unit into digital signals at a predetermined sampling period, a digital delay unit for receiving each of the digital signals and for producing a plurality of delayed signals corresponding to the receiving beams for each of the digital signals, and a first adding unit for adding the delayed signals corresponding to each of the receive beams and to the respective digital signals. The digital delay unit includes a first delay unit for delaying the respective digital signals at a unit delay time same as the sampling period to produce first delayed signals, and a second delay unit for delaying each of the first delayed signals at a unit delay time shorter than the sampling period to produce a plurality of delayed signals for each of the first delayed signals.

11 Claims, 7 Drawing Sheets m=1 m=3 m=5

DIRECTION AND DISTANCE

RECEIVING BEAM FORMER AND AN ULTRASONIC IMAGING SYSTEM USING THE SAME

BACKGROUND OF THE INVENTION

This invention relates to a receiving beamformer capable of simultaneously generating a plurality of receiving beam signals corresponding to the receive beams of a plurality of directions on the basis of a plurality of ultrasonic received signals, and an ultrasonic imaging system, such as an ultrasonic diagnosis equipment, ultrasonic reflectoscope or ultrasonic sonar, which uses this receiving beamformer.

The recent ultrasonic imaging system simultaneously generates a plurality of receiving beam signals corresponding to a plurality of receiving beams of different directions for a single round of ultrasonic wave transmission and reception in order to make high-speed imaging. As this kind of technique, an ultrasonic diagnosis equipment is disclosed in, for example, JP-A-59-49752. FIG. 7 shows the receive beamformer 1 used in this ultrasonic diagnosis equipment. Referring to FIG. 7, there are shown variable amplifiers 2, A/D converters 3, digital delay units 4 and adders 5a, 5b. The variable amplifiers 2 amplify, in accordance with the depth of measurement, the signals $S_1, S_2, \ldots S_n$ which are received on respective channels by an array of vibrator elements of an ultrasonic transmitter/receiver. The output signals from the variable amplifiers 2 are converted into digital signals by the A/D converters 3. The digital signals from the A/D converters 3 are supplied to and arbitrarily delayed by the digital delay units 4, which then produce a plurality of delayed signals $Da_1, Db_1, Da_2, Db_2, \ldots, Da_n, Db_n$. The delayed signals $Da_1, Da_2, \ldots, Da_n$ are supplied to and added by the adder 5a, and the delayed signals $Db_1, Db_2, \ldots, Db_n$ supplied to and added by the adder 5b. As a result of addition, a plurality of adders 5a, 5b simultaneously produce the receiving beam signals Ba, Bb corresponding to the receiving beam signals of a plurality of directions. Each of the digital delay units 4 is formed of a shift register 6 and a plurality of parallel multiplexers 7a, 7b. Each signal delay block, $8_1, 8_2, \ldots, 8_n$, including the variable amplifier 2, the A/D converter 3 and the digital delay unit 4 is provided on each channel for the received signal $S_1$ through $S_n$.

The unit delay time necessary for the generation of receiving beam signals Ba, Bb is selected to be, for example, 10 ns. The A/D converters 3 sample the signals $S_1$ through $S_n$ at a frequency of, for example, 100 MHz, and supply the sampled signals to the shift registers 6 of the respective digital delay units 4. The tap outputs of each of the shift registers 6 are fed to a plurality of the following multiplexers 7a, 7b, which select delay taps corresponding to a plurality of ultrasonic beams of different directions. The multiplexers of the blocks produce the delayed signals $Da_1, Db_1, \ldots, Da_n, Db_n$, which are then supplied to a plurality of adders 5a, 5b, respectively. As a result of addition, the adders produce the receiving beam signals Ba, Bb of a plurality of directions.

SUMMARY OF THE INVENTION

In this conventional receive beamformer 1, however, it is necessary that the sampling period of the A/D converters 3 be made equal to the unit delay time (for example, 10 ns) of the digital delay units 4. Therefore, the A/D converters 3 must be operated at a high sampling frequency of, for example, 100 MHz. In addition, the shift registers 6, multiplexers 7a, 7b and adders 5a, 5b are required to operate at a high speed according to the high-speed A/D converters. Consequently, the receive beamformer 1 becomes a high-speed type as a whole, leading to high cost and large power consumption.

Accordingly, it is an object of the invention to provide a receiving beamformer having low-speed A/D converters and capable of simultaneously generating a plurality of receiving beam signals corresponding to the receiving beams of a plurality of directions on the basis of a plurality of received ultrasonic wave signals, and to provide an ultrasonic imaging system using this receiving beamformer.

To achieve this object, according to one aspect of the invention, there is provided a receiving beamformer for simultaneously generating a plurality of receiving beam signals corresponding to receiving beams of a plurality of directions, respectively on the basis of received signals obtained by an array of vibrator elements for receiving an ultrasonic wave, including: a variable amplifying unit for amplifying the received signals in accordance with the depth of measurement to produce output signals; an A/D converting unit for converting the output signals from the variable amplifying unit into digital signals at a predetermined sampling period, respectively; a digital delay unit for delaying each of the digital signals and for producing a plurality of delayed signals corresponding to the receiving beams, respectively for each of the digital signals; and a first adding unit for adding the delayed signals corresponding to each of the receiving beams and to the respective digital signals; wherein the digital delay unit includes: a first delay unit for delaying the respective digital signals at a unit delay time same as the sampling period, respectively to produce first delayed signals; and a second delay unit for delaying each of the first delayed signals at a unit delay time shorter than the sampling period to produce a plurality of delayed signals for each of the first delayed signals.

In this receiving beamformer, the first delay unit provided within the digital delay unit delays the respective digital signals from the A/D converting unit at a unit delay time same as the sampling period to produce the first delayed signals. The second delay unit delays each of the first delayed signals at a unit delay time shorter than the sampling period to produce a plurality of delayed signals for each of the first delayed signals. Thus, the unit delay time of the second delay unit provided at the output side within the digital delay unit may be selected to be an amount (for example, 10 ns) necessary for the generation of the receive beam signals corresponding to the finally desired ultrasonic wave beam, and hence the first delay unit before the second delay unit may make a longer unit time delay (for example, 40 ns). Therefore, the A/D converting unit before the first delay unit may sample signals at a slow speed according to the unit delay time of the first delay unit. Accordingly, the receiving beamformer can be formed of a low-speed A/D converting unit and a low-speed first delay unit. Thus, this receiving beamformer of low power consumption can be produced at a low cost.

The digital delay unit of the above receiving beamformer may further include a third delay unit for delaying at least one of the plurality of delayed signals produced for each of the first delayed signals by a time corresponding to K (K is an integer of zero or more) times the sampling period. In this case, even if the directional deviation between the receiving beams is large, desired receiving beam signals can be produced.

According to another aspect of the invention, there is provided an ultrasonic imaging system including the above receiving beamformer.

According to still another aspect of the invention, there is provided a receiving beamformer for simultaneously generating a plurality of receiving beam signals corresponding to receiving beams of a plurality of directions, respectively on the basis of received signals obtained by an array of vibrator elements for receiving an ultrasonic wave, including: a variable amplifying unit for amplifying the received signals in accordance with the depth of measurement to produce amplified output signals; an A/D converting unit for converting the output signals from the variable amplifying unit into digital signals at a predetermined sampling period, respectively; a first delay unit for delaying the respective digital signals at a unit delay time same as the sampling period, respectively to produce first delayed signals; a plurality of adder groups respectively associated with the receiving beams, each of the adder groups including a plurality of first adding units associated with a plurality of delay times based on a unit delay time shorter than the sampling period, each of the first adding units adding inputs to produce an output; a plurality of signal distributor groups respectively associated with the first delayed signals, each of the distributor groups including a plurality of signal distributing units respectively associated with the receiving beams, each of the distributing units permitting an input signal to the distributing unit to be selectively distributed to one of the plurality of first adding units included in the adder group associated with the corresponding receiving beam in accordance with the delay time by which the input signal is delayed; an input unit for permitting a signal based on each of the first delayed signals to be supplied to the plurality of signal distributing units included in the adder group associated with each of the first delayed signals; a second delay unit for delaying the output from each of the first adding units by a time corresponding to the delay time associated with each of the first adding units to produce a second delayed signal; and a second adding unit for adding the second delayed signals associated with each of the adder groups.

In this receiving beamformer, the first delay unit provided within the digital delay unit delays the respective digital signals from the A/D converting unit at a unit delay time same as the sampling period to produce first delayed signals. The second delay unit delays the output from each of the first adding units by a time according to a unit delay time shorter than the sampling period to produce a second delayed signal. Thus, this receiving beamformer, like the first mentioned receiving beamformer, can be formed of a low-speed A/D converting unit and so on.

According to further aspect of the invention, there is provided an ultrasonic imaging system including this receiving beamformer.

DESCRIPTION OF THE PREFERRED EMBODIMENTS

A receiving beamformer and ultrasonic imaging system according to the invention will be described with reference to the accompanying drawings.

Figure 1:
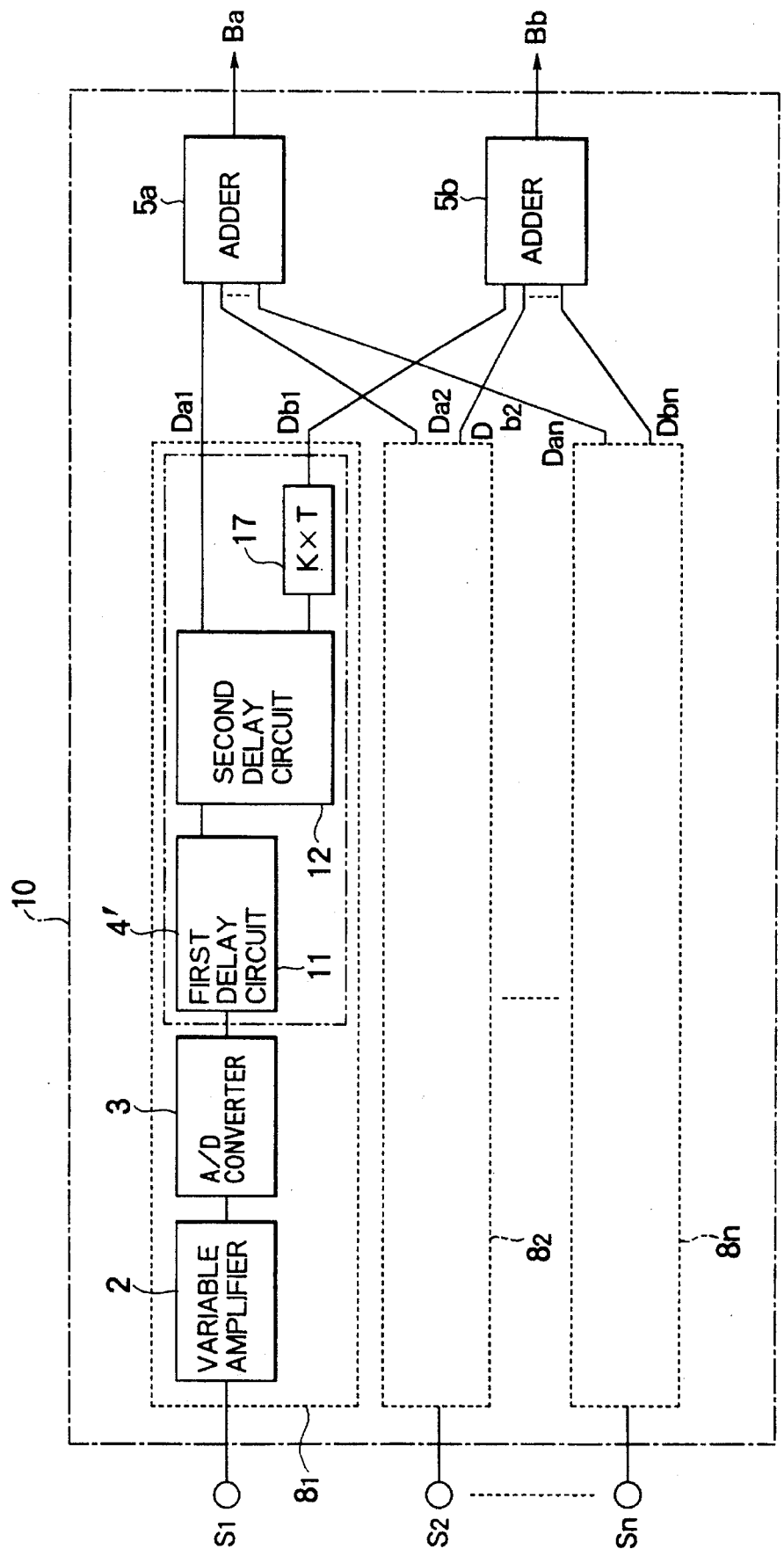
FIG. 1 is a block diagram of a receiving beamformer of one embodiment of the invention.

FIG. 1 is a block diagram of a receiving beamformer 10 of one embodiment of the invention. This receiving beamformer simultaneously produces a plurality of receiving beam signals corresponding to the receive beams of a plurality of directions each time an ultrasonic wave is once transmitted and received. As shown in FIG. 1, the receiving beamformer 10 has variable amplifiers 2, A/D converters 3 and digital delay units 4' provided on the respective channels for the received signals $S_1, S_2, \ldots, S_n$, and for example, two adders 5a, 5b.

The variable amplifiers 2 are supplied with the signals $S_1$ through $S_n$ which are received on channels $8_1$ through $8_n$ by an array of vibrator elements of an ultrasonic wave transmitter/receiver of a probe not shown. The variable amplifiers 2 amplify these signals in accordance with the depth of measurement. Each of the variable amplifiers 2 is formed of, for example, a time gain control amplifier. The A/D converters 3 are supplied with the amplified signals from the amplifiers, and convert the signals into digital signals at a predetermined sampling period T, or for example, at a sampling frequency twice or above higher than the signal frequency band of the signal $S_1$ through $S_n$ received on each channel. The digital delay units 4' arbitrarily delay the digital signals fed from the A/D converters 3 to produce a plurality of, for example, two, delayed signals $Da_1, Db_1$ through $Da_n, Db_n$.

The two adders 5a, 5b are respectively supplied with the delayed signals $Da_1, Db_1$ through $Da_n, Db_n$ from the digital delay units 4'. The adder 5a adds the delayed signals $Da_1, Da_2, \ldots, Da_n$, and the adder 5b adds the delayed signals $Db_1, Db_2, \ldots, Db_n$. As a result of addition, the adders 5a, 5b simultaneously produce, for example, the receiving beam signals Ba, Bb corresponding to the receiving beams of two directions. The signal delay blocks, $8_1, 8_2, \ldots, 8_n$, each of which is formed of the variable amplifier 2, the A/D converter 3 and the digital delay unit 4', are respectively provided on the channels for the received signals $S_1$ through $S_n$.

In this embodiment, each of the digital delay units 4' includes a first delay circuit 11 for delaying the digital signal from the A/D converter 3 at a unit delay time same as the sampling period T, a second delay circuit 12 which is supplied with the output signal from the first delay circuit 11 and which delays this signal at a unit delay time shorter than the sampling period T to produce a plurality of delayed signals $Da_1, Db_1, \ldots, Da_n, Db_n$, and a shift register 17 which will be described later. The first delay circuit 11 is formed of, for example, a shift register or a RAM, and delays the input signal at a unit delay time of the sampling period T for signal collection. The delaying operation is realized by the difference between the writing time and reading time for the received signal from the A/D converter 3. The second delay circuit 12 is supplied with the delayed signal from the first delay circuit 11, and delays this signal at a unit delay time shorter than the sampling period to produce a plurality of delayed signals $Da_1, Db_1, \ldots, Da_n, Dbn$. That is, the second delay circuits 12 perform the second delay operation at a unit delay time necessary for finally making, for example, the receiving beam signals Ba, Bb of two directions. The delay times of the first and second delay circuits 11 and 12 are controlled, for example, dynamically in accordance with the dynamic focus.

Figure 2:
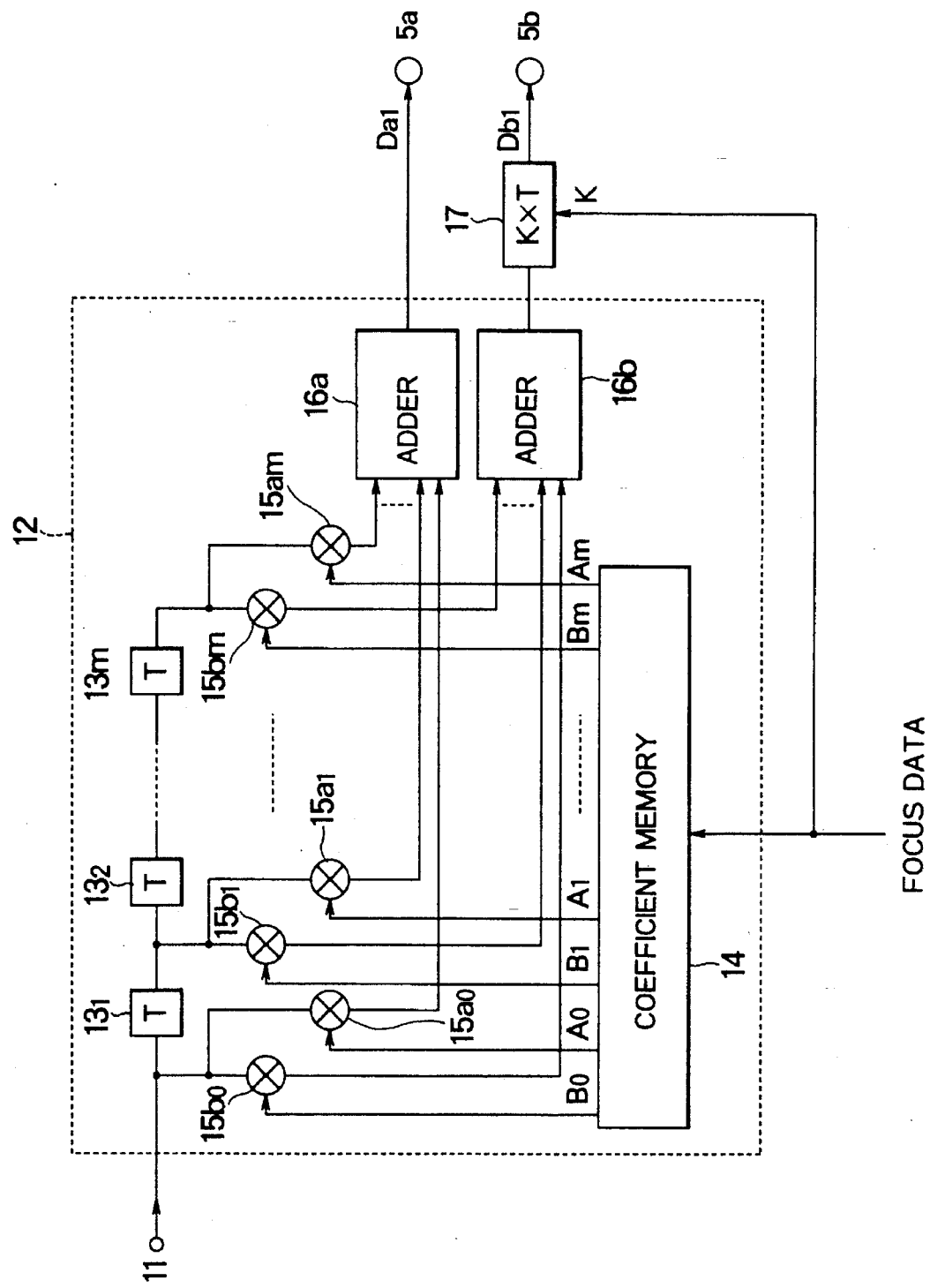
FIG. 2 is a block diagram of an example of the construction of the second delay circuit within the receiving beamformer shown in FIG. 1.

Each of the second delay circuits 12, as shown in FIG. 2, includes a series (m is an integer of one or more) of m shift registers $13_1, 13_2, \ldots, 13_m$ which sequentially shift the signal from the first delay circuit 11 at each sampling period T, a coefficient memory 14 stored therein coefficients $A_0, A_1, \ldots, A_m; B_0, B_1, \ldots, B_m$ (these coefficients are supplied from the outside as focus data) for interpolation delay at a unit delay time shorter than the sampling period T, a plurality of digital multipliers $15a_0, 15b_0, \ldots, 15a_m, 15b_m$ for multiplying the outputs from the m-stage shift registers $13_1$ through $13_m$ by the coefficients $A_0$ through $A_m$, $B_0$ through $B_m$ which correspond to the receiving beams of two directions and which are read from the coefficient memory 14, and adders 16a and 16b for adding the multiplied results from the two groups of digital multipliers, $15a_0$ through $15a_m$, $15b_0$ through $15b_m$. The output signal from the adder 16b is supplied to the shift register 17, where it is delayed by a unit delay time corresponding to the sampling period T. In other words, the shift register 17 delays the output signal from the adder 16b by K times the sampling period T (K is an integer of zero or more). The information of K is supplied as focus data from the outside.

The operation of the receiving beamformer 10 will be mentioned with reference to FIGS. 1 and 2. The signals $S_1$ through $S_n$ received by an array of vibrator elements of an ultrasonic transmitter/receiver unit not shown are supplied to the variable amplifiers 2 of the signal delay blocks $8_1, 8_2, \ldots, 8_n$ on the respective channels. The operation as to the signal on the first channel in FIG. 1 will hereinafter be described. The received signal $S_1$ is amplified by the variable amplifier 2 in accordance with the depth of measurement, and then supplied to the A/D converter 3. This A/D converter 3 samples this signal at a sampling frequency of, for example, 25 MHz, or ½ the signal frequency band of the received signal. The digital signal from the A/D converter 3 is supplied to the first delay circuit 11 of the digital delay unit 4'. This first delay circuit 11 delays this digital signal at a unit delay time of, for example, 40 ns equivalent to the sampling frequency (25 MHz) of the A/D converter 3.

The output signal from the first delay circuit 11 is supplied to the m-stage shift registers $13_1$ through $13_m$ of the second delay circuit 12 shown in FIG. 2, and thus it is shifted by the sampling period T in each shift register. The output signals at the shift register stages $13_1, 13_2, \ldots, 13_m$ are supplied to the two multipliers $15a_0$ through $15a_m$, $15b_0$ through $15b_m$ which correspond to the finally obtained receiving beam signals Ba, Bb of a plurality of directions (for example, two directions). Thus, the input signals to the multipliers are multiplied by the coefficients $A_0$ through $A_m$, $B_0$ through $B_m$ which are read from the coefficient memory 14 in order to make interpolation delaying at a unit delay time (for example, 10 ns) shorter than the sampling period 40 ns. The multiplied results from the two groups of multipliers are respectively supplied to and added by the adders 16a, 16b associated with the receiving beams of the two directions. Thus, the adders 16a, 16b produce interpolation-delayed data (delayed signals) as to a necessary unit delay time (for example, 10 ns). The coefficients stored in the coefficient memory 14 may be the coefficients according to the known SINC function in the sampling theorem. The second delay circuit 12 thus produces the delayed signals $Da_1$, $Db_1$ corresponding to the receiving beams associated with the two directions. If the desired delay time difference between the two delayed signals $Da_1$ and $Db_1$ exceeds the sampling time T, the shift register 17 provided after the adder 16b adds a delay time difference of unit sampling period T to the output of the adder 16b, so that the two delayed signals $Da_1$, $Db_1$ having the desired delay time difference can be produced at the same time. Although desired receiving beam signals can be obtained by the shift registers 17 even when the direction difference between the desired receiving beams is large, the shift register 17 may be removed if the direction difference between the desired receiving beams is small.

The two delayed signals $Da_1$, $Db_1$ are then supplied to the two adders 5a and 5b, respectively as shown in FIG. 1. Similarly, the delayed signals $Da_2, Db_2; \ldots; Da_n, Db_n$ on the channels 2 through n are produced and fed to the two adders 5a and 5b, respectively. The adders 5a, 5b add the delayed signals $Da_1, Da_2, \ldots, Da_n; Db_1, Db_2, \ldots, Db_n$, respectively to produce the two receiving beam signals Ba, Bb of different directions at the same time.

Figure 3A:
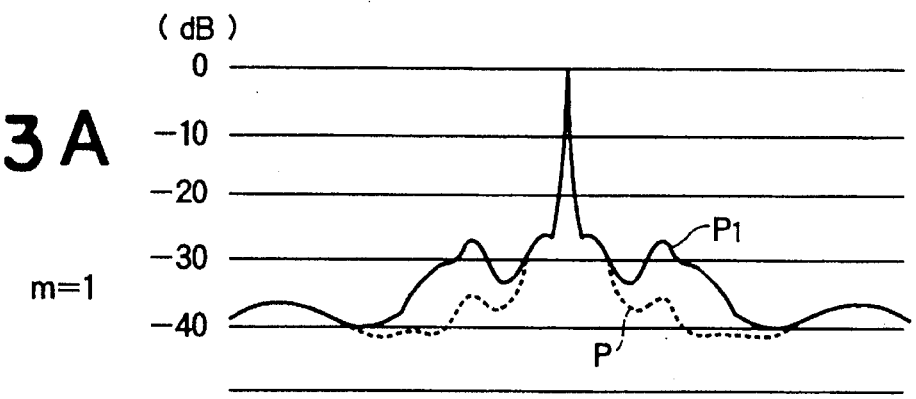
FIGS. 3A, 3B and 3C are graphs showing an example of the results of simulating the patterns of the receiving beams with respect of the number of stages of the shift registers provided within the second delay circuit.
Figure 3B:
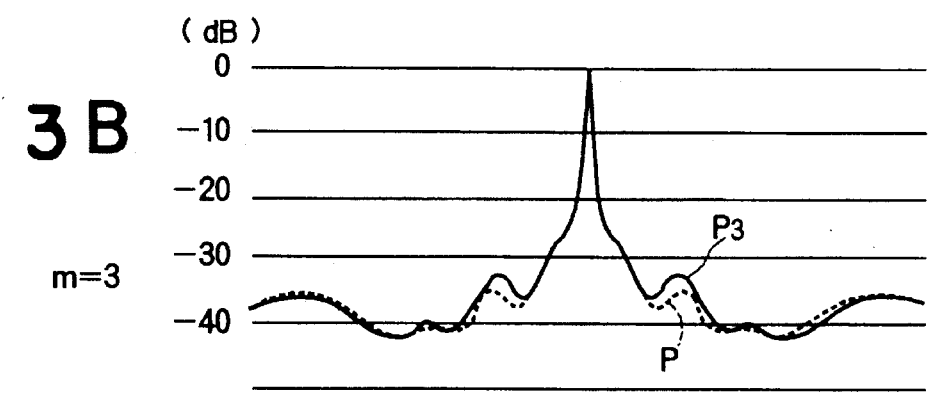
Figure 3C:
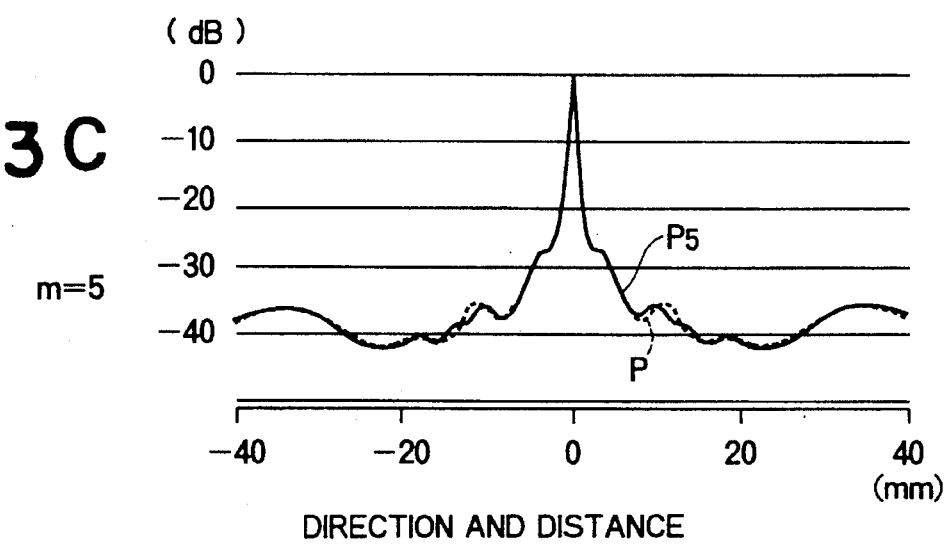

FIGS. 3A, 3B and 3C are graphs showing one example of the result of simulating the patterns of the final receiving beams Ba, Bb according to the number m of stages of shift registers $13_1$ through $13_m$ provided within the second delay circuit 12. In FIGS. 3A, 3B and 3C, the broken-line curves indicate ideal beam patterns when the number m of stages of the shift registers $13_1$ through $13_m$ is infinite, and the solid-line curves indicate beam patterns resulting from interpolation delaying by a certain number of stages, m of shift registers $13_1$ through $13_m$. The solid-line curve in FIG. A shows an example of using only one shift register (m=1), or indicates a beam pattern $P_1$ obtained by interpolation delaying of two samples of the received signal from the shift register $13_1$ in FIG. 2. From FIG. 3A, it will be seen that the S/N ratio is greatly reduced as compared with the ideal broken-line beam pattern P. The solid-line curve in FIG. 3B shows an example of using three shift registers (m=3), or indicates a beam pattern $P_3$ obtained by interpolation delaying of four samples of the received signal from the shift registers $13_1$, $13_2$ and $13_3$ in FIG. 2. From FIG. 3B, it will be seen that the S/N ratio is much improved to approach to the ideal beam pattern P. The solid-line curve in FIG. 3C shows an example of using 5 shift registers (m=5), or indicates a beam pattern $P_5$ obtained by interpolation delaying of six samples of the received signal from the shift registers $13_1, 13_2, \ldots, 13_5$ in FIG. 2. From FIG. 3C, it will be seen that the S/N ratio is greatly improved to almost coincide with the ideal beam pattern P. Therefore, from the result of the simulation, it will be understood that the number m of shift registers $13_1$ through $13_m$ within the second delay circuit 12 is preferably 3 or more. Considering the limit of the circuit scale, particularly 3 through 7 stages are more preferable.

Figure 4:
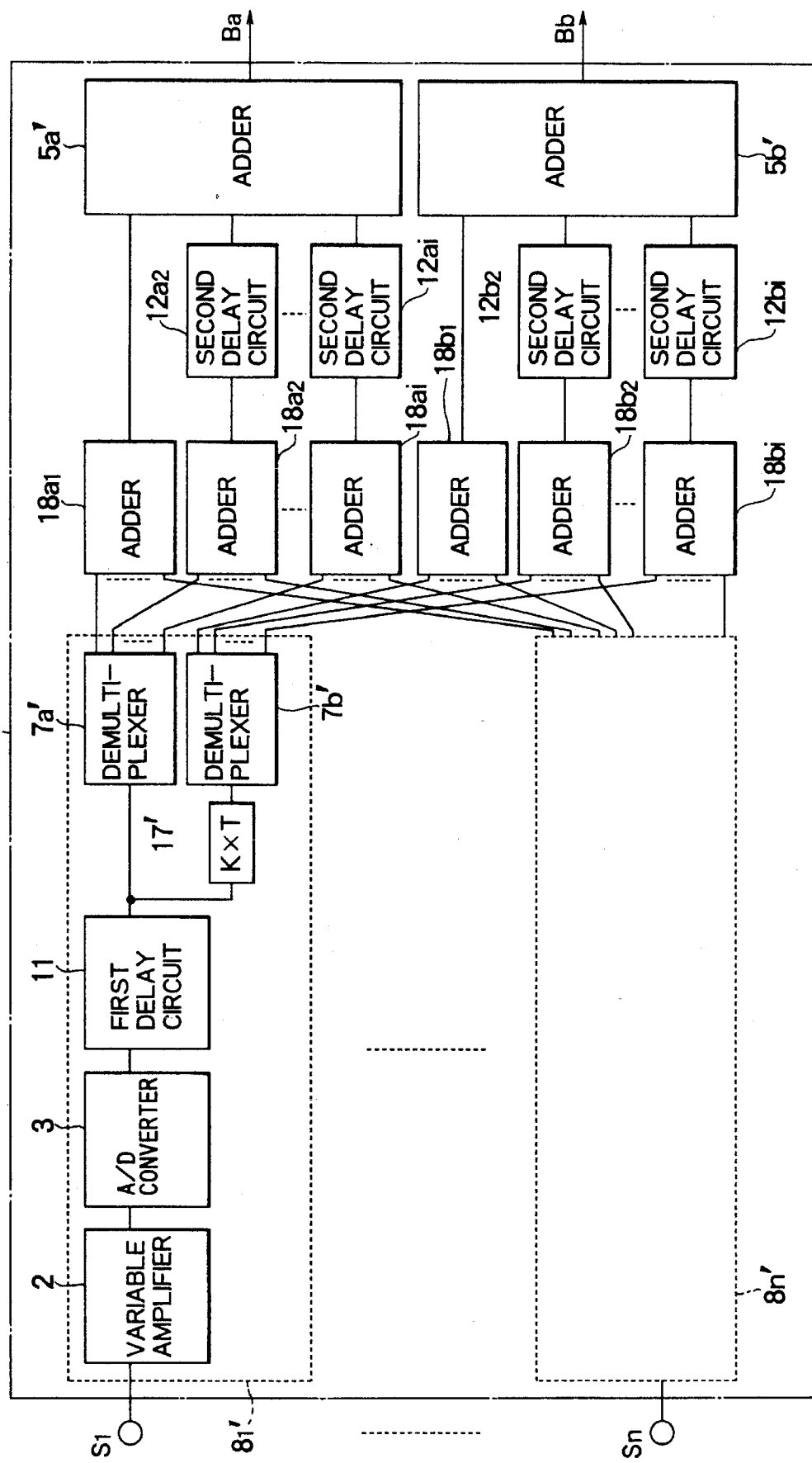
FIG. 4 is a block diagram of a receiving beamformer of another embodiment of the invention.

FIG. 4 is a block diagram of the receiving beamformer of another embodiment of the invention. In this embodiment, demultiplexers 7a', 7b' as signal distributors are provided in parallel after the first delay circuit 11 (the same as the first delay circuit 11 shown in FIG. 1) of each of signal delay blocks $8_1', \ldots, 8_n'$ on the respective channels for the received signals $S_1$ through $S_n$. In addition, a shift register 17' same as the shift register 17 shown in FIG. 2 is provided on the input side of the demultiplexer $7b'$. In addition, after the signal delay blocks $8_1'$ through $8_n'$, first adders $18a_1$ through $18a_i$, and $18b_1$ through $18b_i$ are provided for the two receiving beam signals Ba, Bb of two directions. After these adders, second delay circuits $12a_2$ through $12a_i$, and $12b_2$ through $12b_i$ are provided for the two receiving beam signals Ba, Bb. The two groups of delay circuits, $12a_2$ through $12a_i$, and $12b_2$ through $12b_i$ supply their output signals to two adders $5a'$ and $5b'$, respectively.

Figure 5:
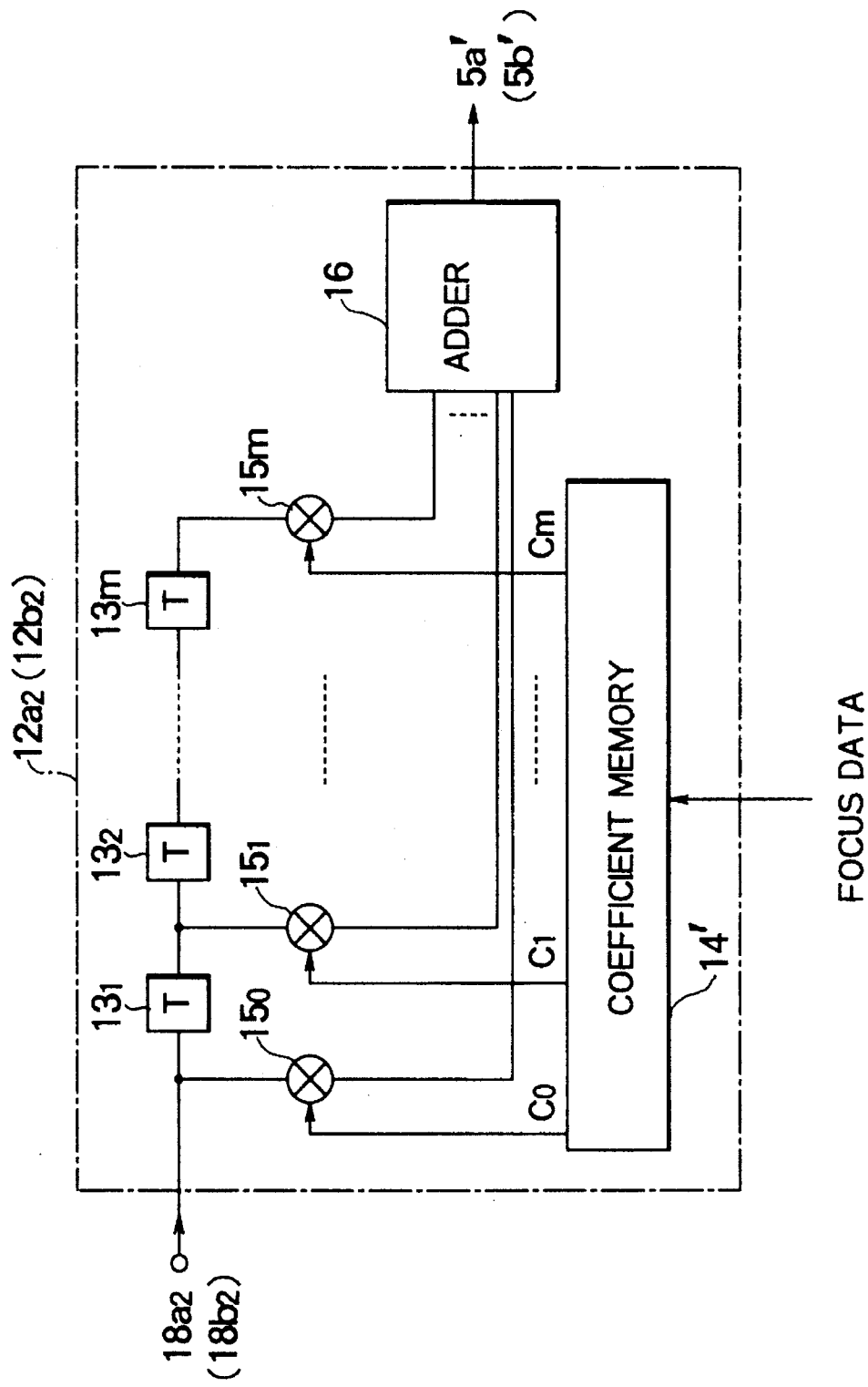
FIG. 5 is a diagram of an example of the construction of the second delay circuit within the receiving beamformer shown in FIG. 4.

Each of the second delay circuits $12a_2$ through $12a_i$ and $12b_2$ through $12b_i$, for example, $12a_2(12b_2)$ as shown in FIG. 5 has m (m is an integer of one or more) shift registers $13_1$ through $13m$ which sequentially shift at each sampling period T the signal fed from the first adder $18a_2$, a coefficient memory $14'$ having stored therein coefficients $C_0, C_1, \ldots, C_m$ for interpolation delay at a unit delay time shorter than the sampling period T, a plurality of digital multipliers $15_0$ through $15_m$ for multiplying the outputs from the m shift registers $13_1$ through $13_m$ by the coefficients $C_0$ through $C_m$ read from the coefficient memory $14'$ for the corresponding receiving beam, and an adder 16 for adding the multiplied results.

In this receiving beamformer $10'$, the demultiplexers $7a'$ and $7b'$ are switched on the basis of the focus data from the outside in order that the output from the first delay circuit 11 can properly be processed in accordance with the amount that it is delayed at a unit delay time shorter than the sampling period T. The outputs from the demultiplexers $7a'$ and $7b'$ are supplied to the groups of first adders, $18a_1$ through $18a_i$, and $18b_1$ through $18b_i$, and added at a shorter unit delay for the respective receiving beams of a plurality of directions. If the unit delay time in the second delay circuits $12a_2$ through $12a_i$, $12b_2$ through $12b_i$ is 10 ns, and if each of the first adders $18a_i$, $18b_i$ is formed of four adders, the first ones $18a_1$ and $18b_1$ of the first adders add the signals on the channels to be delayed by 0 ns, the second ones $18a_2$ and $18b_2$ add the signals on the channels to be delayed by 10 ns, . . . , the fourth ones $18a_i$ and $18b_i$ add the signals on the channels to be delayed by 30 ns. At this time, the demultiplexers $7a'$ and $7b'$ divide the signal from the first delay circuit 11 by four. Therefore, the signal from the first delay circuit 11 may be a signal of a unit delay time of 10 ns×4=40 ns. Thus, the sampling frequency of the A/D converter 3 before the first delay circuit 11 may be, for example, as low as 25 MHz.

The output signals from the first adders $18a_1$ through $18a_i$, and $18b_1$ through $18b_i$ are supplied to the second delay circuits $12a_2$ through $12a_i$, and $12b_2$ through $12b_i$ and delayed at a unit delay time of 10 ns. The outputs from the two groups of the second delay circuits are supplied to and added in phase by the two adders $5a'$ and $5b'$, with the result that the receiving beams Ba, Bb of two directions are produced at the same time. In this case, since the number i of the unit delay time shorter than the sampling period T is generally small as compared with the number n of channels for the received signals $S_1$ through $S_n$, the number of the second delay circuits $12a_i$, $12b_i$ can be decreased as shown in FIG. 4. In addition, as will be obvious from FIG. 5, the number of the digital multipliers $15_0$ through $15_m$ can be decreased as compared with that shown in FIG. 2.

While in the embodiments of FIGS. 1 and 4 only the two receiving beam signals are generated in association with the receiving beams of two directions, this invention can be applied to generate three or more receiving beam signals corresponding to a plurality of receiving beams of three or more directions.

Figure 6:
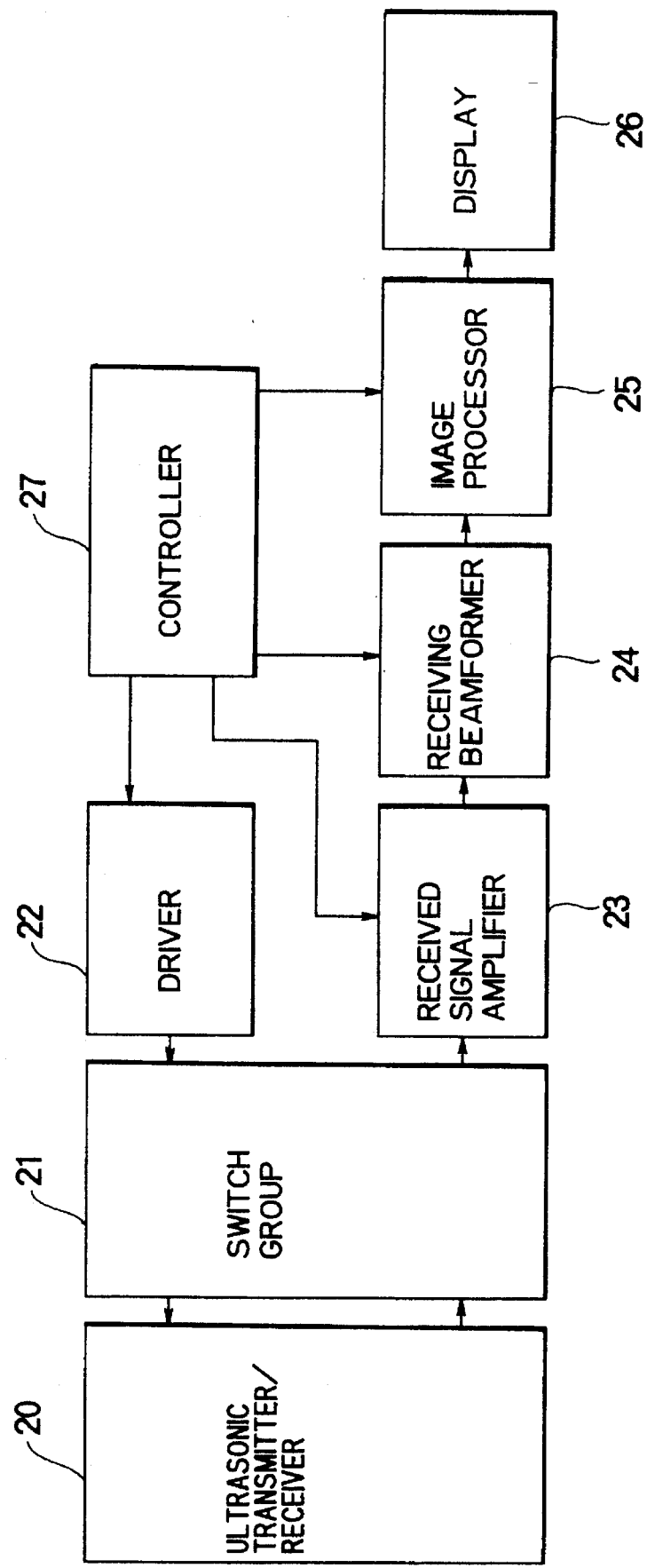
FIG. 6 is a block diagram of an ultrasonic imaging system of still another embodiment of the invention.
Figure 7:
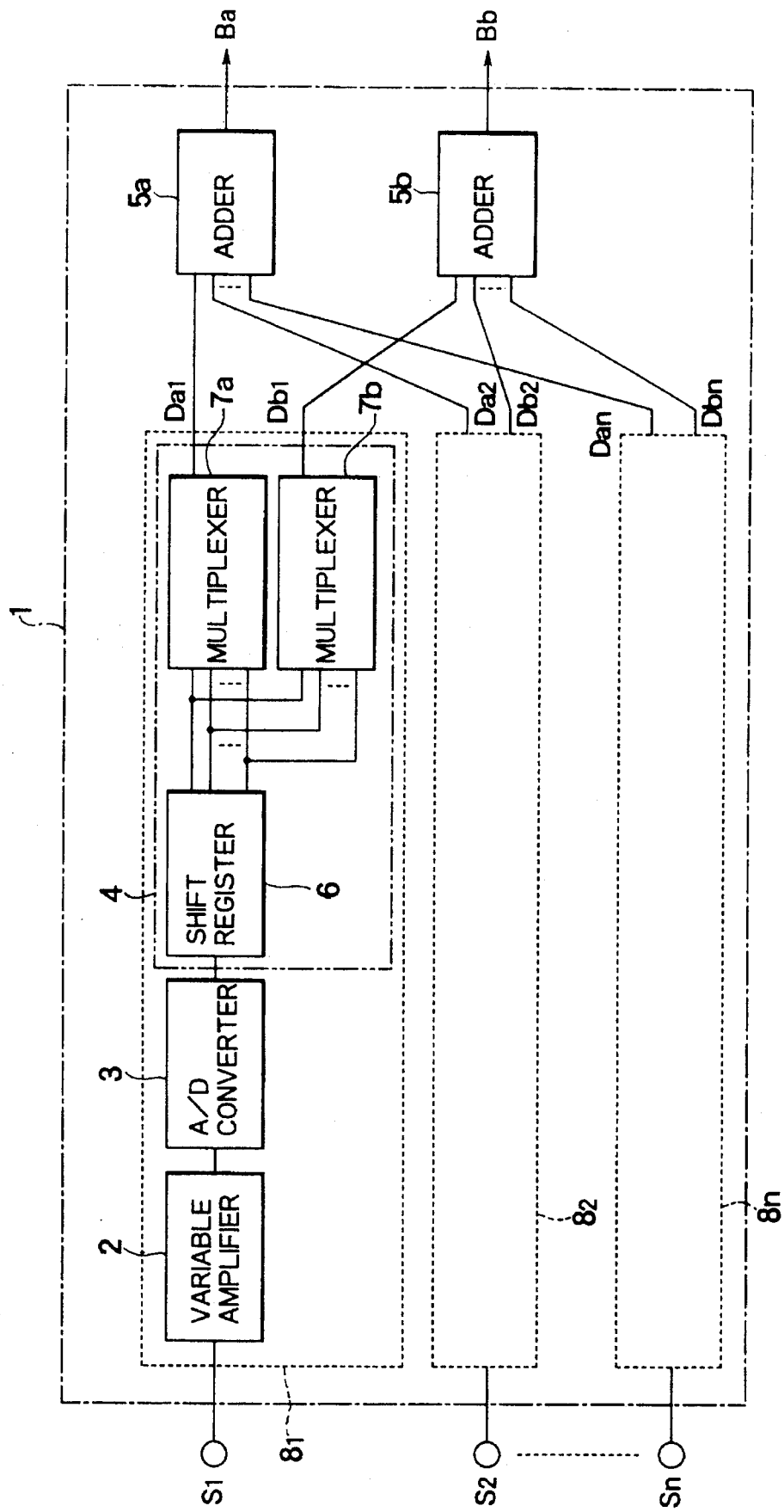
FIG. 7 is a block diagram of a conventional receiving beamformer.

FIG. 6 is a block diagram of an ultrasonic imaging system of still another embodiment of the invention. This ultrasonic imaging system is, for example, an ultrasonic diagnosis equipment for generating a tomographic image of a part of the body to be diagnosed and displaying it by use of an ultrasonic wave. This equipment is of, for example, the electronic scanning type. This ultrasonic imaging system has an ultrasonic transmitter/receiver 20 such as a probe, which has an array of a plurality of strip-shaped vibrator elements and transmits and receives an ultrasonic wave, a switch group 21 for successively selecting only one group of the vibrator elements of this ultrasonic transmitter/receiver 20 and varying the aperture, a driver 22 for driving the vibrator elements of the ultrasonic transmitter/receiver 20 to permit to transmit an ultrasonic wave, a received signal amplifier 23 for amplifying the signals received by the vibrator elements, a receiving beamformer 24 which controls the amplitudes and phases of the output signals from the amplifier 23 to thereby generate receiving beam signals corresponding to receiving beams of a plurality of directions, an image processor 25 for processing the receiving beam signals from the receiving beamformer 24 to produce an image signal, and a display 26 for displaying an image corresponding to the image signal from the image processor 25. In addition, as shown in FIG. 6, a control circuit 27 such as a CPU (central processing unit) is provided for controlling the operation of the above elements of the ultrasonic imaging system.

In this embodiment, the receiving beamformer 24 is the receiving beamformer 10 shown in FIG. 1 or the receiving beamformer $10'$ shown in FIG. 4. Thus, an ultrasonic diagnosis equipment of small power consumption can be realized at a low cost by using the receiving beamformer 10 or $10'$ which is formed of low-speed A/D converters and low-speed digital delay units. This invention is not limited to the ultrasonic diagnosis equipment for medical use shown in FIG. 6, but can be applied to other ultrasonic imaging systems such as ultrasonic reflectoscopes and ultrasonic sonars.

What is claimed is:

1. A receiving beamformer for simultaneously generating a plurality of receiving beam signals corresponding to receiving beams of a plurality of directions, respectively on the basis of received signals obtained by an array of vibrator elements for receiving an ultrasonic wave, said receiving beamformer comprising:

variable amplifying means for amplifying said received signals in accordance with a depth of measurement to produce output signals;

A/D converting means for converting said output signals from said variable amplifying means into digital signals at a predetermined sampling period, respectively;

digital delay means for receiving each of said digital signals and for producing a plurality of delayed signals corresponding to said receiving beams, respectively for each of said digital signals; and first adding means for adding said delayed signals corresponding to each of said receiving beams and to respective said digital signals;

wherein said digital delay means includes:

first delay means for delaying said respective digital signals at a unit delay time same as said sampling period, respectively to produce first delayed signals; and second delay means for delaying each of said first delayed signals at a unit delay time shorter than said sampling period to produce a plurality of delayed signals for each of said first delayed signals.

2. A receiving beamformer according to claim 1, wherein said digital delay means further includes third delay means for delaying at least one of said plurality of delayed signals produced for each of said first delayed signals by a time corresponding to K (K is an integer of zero or more) times said sampling period.

3. A receiving beamformer for simultaneously generating a plurality of receiving beam signals corresponding to receiving beams of a plurality of directions, respectively on the basis of received signals obtained by an array of vibrator elements for receiving an ultrasonic wave, said receiving beamformer comprising:

variable amplifying means for amplifying said received signals in accordance with a depth of measurement to produce output signals;

A/D converting means for converting said output signals from said variable amplifying means into digital signals at a predetermined sampling period, respectively;

digital delay means for receiving each of said digital signals and for producing a plurality of delayed signals corresponding to said receiving beams, respectively for each of said digital signals; and first adding means for adding said delayed signals corresponding to each of said receiving beams and to respective said digital signals;

wherein said digital delay means includes:

first delay means for delaying said respective digital signals at a unit delay time same as said sampling period, respectively to produce first delayed signals; and second delay means for delaying each of said first delayed signals at a unit delay time shorter than said sampling period to produce a plurality of delayed signals for each of said first delayed signals;

wherein said second delay means includes:

shift register means of m stages (m is an integer of one or more) for sequentially shifting one of said first delayed signals at said sampling period;

first multiplying means for multiplying said one of said first delayed signals and the outputs from respective said stages of said shift register means by coefficients of a first group respectively;

second multiplying means for multiplying said one of said first delayed signals and the outputs from respective said stages of said shift register means by coefficients of a second group, respectively;

second adding means for adding the outputs from said first multiplying means; and third adding means for adding the outputs from said second multiplying means.

4. A receiving beamformer according to claim 3, wherein said digital delay means further includes third delay means for delaying the output from said third adding means by a time corresponding to K (K is an integer of zero or more) times said sampling period.

5. A receiving beamformer according to claim 3, wherein the number m of said stages is 3 or more.

6. A receiving beamformer for simultaneously generating a plurality of receiving beam signals corresponding to receiving beams of a plurality of directions, respectively on the basis of received signals obtained by an array of vibrator elements for receiving an ultrasonic wave, said receiving beamformer comprising:

variable amplifying means for amplifying said received signals in accordance with a depth of measurement to produce output signals;

A/D converting means for converting said output signals from said variable amplifying means into digital signals at a predetermined sampling period, respectively;

first delay means for delaying said respective digital signals at a unit delay time same as said sampling period, respectively to produce first delayed signals;

a plurality of adder groups respectively associated with said receiving beams, each of said adder groups including a plurality of first adding means associated with a plurality of delay times based on a unit delay time shorter than said sampling period, each of said first adding means adding inputs to produce an output;

a plurality of signal distributor groups respectively associated with said first delayed signals, each of said distributor groups including a plurality of signal distributing means respectively associated with said receiving beams, each of said distributing means permitting an input signal to said distributing means to be selectively distributed to one of said plurality of first adding means included in said adder group associated with the corresponding receiving beam in accordance with the delay time by which said input signal is delayed;

input means for permitting a signal based on each of said first delayed signals to be supplied to said plurality of signal distributing means included in said adder group associated with each of said first delayed signals;

second delay means for delaying said output from each of said first adding means by a time corresponding to said delay time associated with each of said first adding means to produce a second delayed signal; and second adding means for adding said second delayed signals associated with each of said adder groups.

7. A receiving beamformer according to claim 6, wherein said input means includes third delay means for delaying each of said first delayed signals by a time corresponding to K (K is an integer zero or more) times said sampling period, and said input means permits an output signal from said third delay means to be fed to at least one of said plurality of signal distributing means included in said adder group associated with each of said first delayed signals.

8. A receiving beamformer according to claim 6, wherein said second delay means includes:

shift register means of m stages (m is an integer of one or more) for sequentially shifting said output of one of said plurality of first adding means at said sampling period;

multiplying means for multiplying said output of said one of said plurality of first adding means and the outputs of respective said stages of said shift register means by coefficients of one group, respectively; and third adding means for adding the outputs from said multiplying means.

9. A receiving beamformer according to claim 8, wherein the number m of said stages is 3 or more.

10. An ultrasonic imaging system comprising:

ultrasonic transmitter/receiver means having an array of a plurality of vibrator elements for transmitting and receiving an ultrasonic wave;

driving means for driving said vibrator elements of said ultrasonic transmitter/receiver means to permit to transmit the ultrasonic wave;

amplifying means for amplifying signals received by said vibrator elements;

a receiving beamformer for controlling amplitudes and phases of output signals from said amplifying means to generate a plurality of receiving beam signals corresponding to receiving beams of a plurality of directions;

an image processor for processing said receiving beam signals from said receiving beamformer to produce an image signal; and a display for displaying an image corresponding to said image signal from said image processor;

wherein said receiving beamformer includes;

variable amplifying means for amplifying said received signals in accordance with a depth of measurement to produce output signals;

A/D converting means for converting said output signals from said variable amplifying means into digital signals at a predetermined sampling period, respectively;

digital delay means for receiving each of said digital signals and for producing a plurality of delayed signals corresponding to said receiving beams, respectively for each of said digital signals; and first adding means for adding said delayed signals corresponding to each of said receiving beams and to respective said digital signals;

said digital delay means including:

first delay means for delaying said respective digital signals at a unit delay time same as said sampling period, respectively to produce first delayed signals; and second delay means for delaying each of said first delayed signals at a unit delay time shorter than said sampling period to produce a plurality of delayed signals for each of said first delayed signals.

11. An ultrasonic imaging system comprising:

ultrasonic transmitter/receiver means having an array of a plurality of vibrator elements for transmitting and receiving an ultrasonic wave;

drive means for driving said vibrator elements of said ultrasonic transmitter/receiver means to permit to transmit the ultrasonic wave;

amplifying means for amplifying signals received by said vibrator elements;

a receiving beamformer for controlling amplitudes and phases of output signals from said amplifying means to generate a plurality of receiving beam signals corresponding to receiving beams of a plurality of directions;

an image processor for processing said receiving beam signals from said receiving beamformer to produce an image signal; and a display for displaying an image corresponding to said image signal from said image processor;

wherein said receiving beamformer includes;

variable amplifying means for amplifying said received signals in accordance with a depth of measurement to produce amplified output signals;

A/D converting means for converting said output signals from said variable amplifying means into digital signals at a predetermined sampling period, respectively;

first delay means for delaying said respective digital signals at a unit delay time same as said sampling period, respectively to produce first delayed signals;

a plurality of adder groups respectively associated with said receiving beams, each of said adder groups including a plurality of first adding means associated with a plurality of delay times based on a unit delay time shorter than said sampling period, each of said first adding means adding inputs to produce an output;

a plurality of signal distributor groups respectively associated with said first delayed signals, each of said distributor groups including a plurality of signal distributing means respectively associated with said receiving beams, each of said distributing means permitting an input signal to said distributing means to be selectively distributed to one of said plurality of first adding means included in said adder group associated with the corresponding receiving beam in accordance with the delay time by which said input signal is delayed;

input means for permitting a signal based on each of said first delayed signals to be supplied to said plurality of signal distributing means included in said adder group associated with each of said first delayed signals;

second delay means for delaying said output from each of said first adding means by a time corresponding to said delay time associated with each of said first adding means to produce a second delayed signal; and second adding means for adding said second delayed signals associated with each of said adder groups.

* * * * *